(12) United States Patent
Lusso et al.

(10) Patent No.: US 6,709,649 B1
(45) Date of Patent: Mar. 23, 2004

(54) RANTES DERIVED PEPTIDES WITH ANTI-HIV ACTIVITY

(75) Inventors: Paolo Lusso, Milan (IT); Vincenzo Pavone, Naples (IT)

(73) Assignees: Fondazione Centro San Raffaele Del Monte Tabor, Milan (IT); PRIMM S.r.l., Milan (IT)

( * ) Notice: Subject to any disclaimer, the term of this patent is extended or adjusted under 35 U.S.C. 154(b) by 0 days.

(21) Appl. No.: 09/831,500

(22) PCT Filed: Nov. 11, 1999

(86) PCT No.: PCT/EP99/08651

§ 371 (c)(1),
(2), (4) Date: Jun. 22, 2001

(87) PCT Pub. No.: WO00/27880

PCT Pub. Date: May 18, 2000

(30) Foreign Application Priority Data

Nov. 11, 1998 (IT) .......................................... MI98A2441

(51) Int. Cl.⁷ .............................................. A61K 38/19
(52) U.S. Cl. .............................. 424/85.1; 514/2; 514/8; 514/13; 530/326
(58) Field of Search ................................. 530/326, 350; 424/85.1; 514/2, 8, 13

(56) References Cited

U.S. PATENT DOCUMENTS 6,159,711 A * 12/2000 Proudfoot et al. ......... 435/69.5

FOREIGN PATENT DOCUMENTS

| WO | WO97/19696 | 6/1997 |
| WO | WO98/51705 | 11/1998 |
| WO | WO99/11666 | 3/1999 |

* cited by examiner

Primary Examiner—Prema Mertz
(74) Attorney, Agent, or Firm—Nixon & Vanderhye, P.C.

(57) ABSTRACT

Peptides having 12 to 30 amino acids with sequence homologous or corresponding to the sequence 1o–34 of RANTES having inhibitory activity against the human immunodeficiency virus (HIV) as well as anti-allergic and antiinflamatory activity.

4 Claims, No Drawings

SEQUENCE LISTING

```
<160> NUMBER OF SEQ ID NOS: 22

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 1

Phe Ala Tyr Ile Ala Arg Pro Leu Pro Arg Ala His Ile Lys Glu Tyr
  1               5                  10                  15

Phe Tyr

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 2

Cys Phe Ala Tyr Ile Ala Arg Pro Leu Pro Arg Ala His Ile Lys Glu
  1               5                  10                  15

Tyr Phe Tyr

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 3

Phe Ala Tyr Ile Ala Arg Pro Leu Pro Arg Ala His Ile Lys Glu Tyr
  1               5                  10                  15

Phe Tyr

<210> SEQ ID NO 4
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      RANTES-Derived Peptide
<223> OTHER INFORMATION: C-term Amidation

<400> SEQUENCE: 4

Cys Phe Ala Tyr Ile Ala Arg Pro Leu Pro Arg Ala His Ile Lys Glu
  1               5                  10                  15

Tyr Phe Tyr

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 5

Cys Phe Ala Tyr Ile Ala Arg Pro Leu Pro Arg Ala His Ile Lys Glu
  1               5                  10                  15

Tyr Phe Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 6

Tyr Phe Tyr Glu Lys Ile His Ala Arg Pro Leu Pro Arg Ala Ile Tyr
  1               5                  10                  15

Ala Phe Cys

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 7

Tyr Phe Tyr Glu Lys Ile His Ala Arg Pro Leu Pro Arg Ala Ile Tyr
  1               5                  10                  15

Ala Phe Cys

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 8

Phe Ala Tyr Ile Ala Arg Pro Leu Pro Arg Ala His Ile Lys Glu Tyr
  1               5                  10                  15

Phe
```

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 9

Ala Tyr Ile Ala Arg Pro Leu Pro Arg Ala His Ile Lys Glu Tyr
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 10

Cys Phe Ala Tyr Ile Ala Arg Pro Leu Pro Arg Ala His Ile Lys
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 11

Cys Phe Ala Tyr Ile Ala Arg Pro Leu Pro Arg Ala His Ile Lys Glu
 1               5                  10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 12

Phe Ala Tyr Ile Ala Arg Pro Leu Pro Arg Ala His Ile Lys
 1               5                  10

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 13

Pro Cys Cys Phe Ala Tyr Ile Ala Arg Pro Leu Pro Arg Ala His Ile
 1               5                  10                  15

Lys Glu

<210> SEQ ID NO 14

```
<211> LENGTH: 18
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 14

Tyr Ile Ala Arg Pro Leu Pro Arg Ala His Ile Lys Glu Tyr Phe Tyr
 1               5                  10                  15

Thr Ser

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 15

Cys Phe Ala Tyr Ile Ala Arg Pro Leu Pro Arg Ala His
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 16

Cys Phe Ala Tyr Ile Ala Arg Pro Leu Pro Arg Ala
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 17

Phe Ala Tyr Ile Ala Arg Pro Leu Pro Arg Ala His
 1               5                  10

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 18

Cys Cys Phe Ala Tyr Ile Ala Arg Pro Leu Pro Arg Ala His Ile Lys
 1               5                  10                  15

Glu Tyr

<210> SEQ ID NO 19
```

-continued

```
<211> LENGTH: 24
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 19

Cys Phe Ala Tyr Ile Ala Arg Pro Leu Pro Arg Ala His Ile Lys Glu
  1               5                  10                  15

Tyr Phe Tyr Thr Ser Gly Lys Cys
             20

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 20

Tyr Phe Tyr Thr Ser Gly Lys Cys Ser Asn Pro Ala
  1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 21

Tyr Thr Ser Gly Lys Cys Ser Asn Pro Ala Val Val
  1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      RANTES-Derived Peptide
<223> OTHER INFORMATION: C-term Amidation

<400> SEQUENCE: 22

Ser Gly Lys Cys Ser Asn Pro Ala Val Val Phe Val
  1               5                  10
```

RANTES DERIVED PEPTIDES WITH ANTI-HIV ACTIVITY

The present invention relates to RANTES-derived peptides having inhibitory activity against the human immunodeficiency virus (HIV).

The peptides of the invention are useful for the treatment of diseases which are connected with the infection of viruses like HIV-1, other primate-lentiretroviruses (HIV-2, SIV) and other viruses which use chemokine receptors to bind the cellular surface and/or to penetrate the target cell, as well as for the treatment of all the diseases, like the allergic or autoimmune diseases, in the pathogenesis of which chemokines play an important role.

BACKGROUND OF THE INVENTION

The term chemokine is used to identify a family of chemotactic cytokines characterized by a high degree of genetic, structural and functional similarity (Immunol. Today 1993, 14:24).

Most known chemokines are grouped in two main families referred to as C-X-C and C-C, depending on the configuration of a conserved motif of two cysteine in their sequence (Ann. Rev. Immunol. 1994, 55:97–179).

Chemokines are important mediators of the inflammatory response which act through the recruitment of specific cellular populations of the immune system in the inflammatory site; the C-X-C chemokines are generally active on neutrophil granulocytes while the C-C chemokines are active on eosinophil and basophil granulocytes, on limphocytes and monocytes.

RANTES, MIP-1α and MIP-1β are C-C chemokines which have been proposed as possible mediators of autoimmune and allergic diseases.

Recently, a specific antiviral effect against primate lentiretrovirus has been described for those three chemokines (Science, 1995, 270:1811–1815).

RANTES is the most potent among C-C chemokines which inhibit the HIV infection. This chemokine bonds to the CCR5 receptor, which is the main membrane co-receptor for HIV-1, in that it is used by most viral strains present in the population and preferably sexually transmitted. Said receptor is therefore a primary target for possible therapeutical strategies, above all during the asymptomatic phase of HIV disease. However, the therapeutic use of natural chemokines is hampered by their pro-inflammatory activity, in that most chemokines are involved in leucocyte recruitment at the inflammation and infection sites, and in their functional activation.

At the moment a preliminary knowledge exists of the domains involved in the pro-inflammatory activity of some chemokines, but not of the domains involved in the antiviral activity. A number of recent studies have suggested that an element crucial for the chemokineinduced receptor activation is located at the molecule's $NH_2$-terminus (J. Biol. Chem. 1991; 266:23128–23134; Biochem. Biophys. Comm. 1995, 211:100–105). Actually, a preliminary study (Nature, 1996, 383:400) and a more detailed study (Science; 1997, 276:282), both recently published, have shown that RANTES-chemokine analogues modified at the $NH_2$ terminus (through the deletion of 8 amino acids, or through the covalent bond of a complex chemical radical [amino-oxypentane or AOP], respectively) maintain the anti-HIV activity even though they do not induce chemotaxis in vitro or they induce it to a very low extent.

Peptides corresponding to the sequences 7–68 to 10–68 of RANTES are disclosed in WO97/44462. RANTES mutants such as Leu-RANTES and Met-RANTES are disclosed in WO96/17935 and WO98/13495. However, in therapeutical applications, the use of small molecules or peptides is preferred, compared with the whole protein, although in the recombinant form, for a number of reasons, such as easiness of synthesis and possibility of minimizing any side-effects caused by the molecule regions which are not useful or even harmful. A number of examples of peptides in the preclinical phase for anti-HIV therapy can, in fact, be found in literature: 1) Judice et al., PNAS 94:13426,1997, disclose structurally rigid peptides deriving from the gp41 sub-unit of HIV envelope, which inhibit the fusion of the cell membraneo 2) Prieto et al., AIDS Res Hum Retroviruses 12:1023, 1996, disclosed modified peptides (benzyl-conjugated) deriving from CD4; or 3) Robinson et al., J Leuk Biol 63:94, 1998, disclose the activity of Indolicin 13-mer, a natural peptide of bovine origin, neutrophil and capable of inhibiting HIV virus at doses comprised from 60 to 100 μM; 4) Heveker et al., Curr Biol 8:369, 1998: describe peptides deriving from the N-terminus of SDF-1, capable of inhibiting HIV and which also lack the pro-inflammatory activity when the first two amino acids are deleted.

DISCLOSURE OF THE INVENTION

It has now been found that RANTES-derived peptides are particularly active in inhibiting HIV viral infection.

The peptides of the invention have 12 to 30 amino acids with sequence identical to a portion of at least 5 consecutive aminoacids of the sequence 9–38 of RANTES.

The peptides of the invention consist of either natural amino acids of the D or L series or of modified or "non-protein" amino acids.

Preferably, the peptides of the invention have from 15 to 35 amino acids, more preferably from 18 to 25 amino acids.

Preferably, the peptides of the invention have a sequence derived from or identical to at least 10 consecutive amino acids of the sequence 9–38 of RANTES, more preferably derived from or identical to at least 12 amino acids and even more preferably derived from or identical to at least 15 amino acid, the other amino acids in the peptide sequence deriving from conservative substitutions of the natural amino acids in the native sequence of RANTES.

The sequence identity of the peptides of the invention with the above mentioned RANTES regions, for example the sequence comprised between the amino acid in position 9 and the amino acid in position 38 of the RANTES native sequence, is preferably of at least 50%, preferably at least 80% and more preferably of at least 90%.

The substitutions of the natural amino acids of the native sequence are preferably of conservative type, both with other natural amino acids and with non-proteic amino acids. "Conservative substitution " herein means, for example, the substitution of a hydrophobic amino acid with another hydrophobic amino acid, of a basic amino acid with another basic amino acid and so on.

"Derived from " means that the native sequence may be further modified by substituting the natural amino acid with the corresponding amino acid of the D series or with non-protein amino acid and/or by inverting the sequence from the carboxy-terminus to the N-terminus and/or by forming dimers through cysteine disulfide bonds and/or by single deletion of amino acids of the native sequence. The invention also refers to peptides having two or more of the above characteristics sequences or domains linked by a suitable linker, e.g. an hydrophilic linker or a metabolic resistant linker. Said derivatives are obtainable according to known methods and criteria.

The invention also provides derivatives of said peptides, chemically modified in order to increase their in vivo stability.

According to a further aspect, the invention provides chimeric proteins which are obtained through conventional techniques by inserting the antiviral domains described above into proteins showing the desired biological characteristics.

Finally, the invention provides antiviral, antiinflammatory and antiallergic pharmaceutical compositions containing the above defined peptides or proteins as the active ingredient.

Preferred peptides of the invention have the following general formula (I):

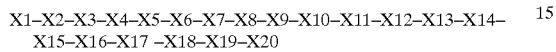

wherein:
- X1=H, Ace, or any amino acid both N-acylated and non-acylated, or a dipeptide of sequence Y1–Y2 both N-acylated and non-acylated in which Y1 and Y2, are the same or different and represent any amino acid;
- X2=any hydrophobic amino acid;
- X3=Ala, Pro, Val, Thr, Ile, thioproline, hydroxyproline;
- X4=any hydrophobic amino acid;
- X5=any hydrophobic amino acid;
- X6=Ala, Pro, Val, Thr, Ile, thioproline, hydroxyproline;
- X7=any basic amino acid;
- X8=Pro, Val, Thr, Ile, thioproline, hydroxyproline;
- X9=Leu, Ile, Val, Thr, Chg, Cha;
- X10=Pro, Val, Thr, Ile, thioproline, hydroxyproline;
- X11=any basic amino acid;
- X12=Ala, Aib, Ser, Gly;
- X13=any basic amino acid;
- X14=any hydrophobic amino acid;
- X15=any basic amino acid;
- X16=any amino acid;
- X17=any hydrophobic amino acid;
- X18=any hydrophobic amino acid;
- X19=any hydrophobic amino acid;
- X20=OH, $NH_2$, Gly, or any hydrophobic amino acid.

Particularly preferred are compounds wherein: X1=H, Ace, Gly, Phe, Cha, Tyr, 1Nal, 2Nal, Trp, Asn, Cys, Ace-Cys, or a dipeptide of sequence Y1–Y2, both N-acylated and non-acylated, wherein Y1 and Y2 are the same or different and represent any amino acid;
- X2=Phe, Cha, Tyr, 1Nal, 2Nal, Trp;
- X3=Ala, Pro, Val, Thr, Ile;
- X4=Tyr, Phe, Cha, 1Nal, 2Nal, Trp;
- X5=Ile, Leu, Val, Thr, 1Nal, 2Nal, Phe, Tyr, Trp;
- X6=Ala, Pro, Val, Thr, Ile;
- X7=Lys, Arg, His, Orn, Dab, Dap, Pba;
- X8=Pro, Val, Thr, Ile;
- X9=Leu, Ile, Val, Thr, Chg, Cha;
- X10=Pro, Val, Thr, Ile;
- X11=Lys, Arg, His, Orn, Dab, Dap, Pba;
- X12=Ala, Aib, Ser, Gly;
- X13=Lys, Arg, His, Orn, Dab, Dap, Pba;
- X14=Ile, Phe, Tyr, Trp, 1Nal, 2Nal, Cha, Leu;
- X15=Lys, Arg, His, Orn, Dab, Dap, Pba;
- X16=any amino acid;
- X17=Tyr, Ile, Phe, Trp, 1Nal, 2Nal, Cha, Leu;
- X18=Phe, Ile, Tyr, Trp, 1Nal, 2Nal, Cha, Leu;
- X19=Tyr, Ile, Phe, Trp, 1Nal, 2Nal, Cha, Leu;
- X20=OH, NH2, Gly, Phe, Tyr, Trp, 1Nal, 2Nal.

Further particularly preferred peptides are those wherein:
- X1=H, Ace, Cys, Ace-Cys;
- X2=Phe, Cha, Tyr;
- X3=Ala, Pro;
- X4=Tyr, Phe, Cha;
- X5=Ile, Leu, Val;
- X6=Ala, Pro, Val;
- X7=Lys, Arg, His, Orn;
- X8=Pro, Val;
- X9=Leu, Ile;
- X10=Pro, Val;
- X11=Lys, Arg, His, Orn;
- X12=Ala, Aib, Ser, Gly;
- X13=Lys, Arg, His, Orn;
- X14=Ile, Phe, Tyr, Trp, Cha, Leu;
- X15=Lys, Arg, Orn, Dab, Dap, Pba;
- X16=Glu, Asp;
- X17=Tyr, Ile, Phe, Trp, 1Nal, 2Nal;
- X18=Phe, Ile, Tyr, Trp, 1Nal, 2Nal, Leu;
- X19=Tyr, Ile, Phe, 1Nal, 2Nal, Cha, Leu;
- X20=OH, $NH_2$, Gly, Phe, Tyr, Trp.

The above amino acid belong to the L or D isomers of both natural amino acids and "non-proteic" amino acids conventionally used in peptide synthesis for the preparation of synthetic analogues of natural peptides. α-Amino acids substituted and non-substituted at the α and β positions of both L and D configuration and α–β unsaturated amino acids are indicated among the non-proteic amino acids.

The natural amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, lysine.

Examples of "non-proteic" amino acids are norleucine, norvaline, alloisoleucine, naphthyl-alanine (1Nal), 2-naphthyl-alanine (2Nal) allothreonine, homoarginine, thioproline, dehydroproline, hydroxyproline, pipecolic acid, azetidinic acid, homoserine, cyclohexylglycine (Chg), (α-amino-n-butyric acid (Aba), cyclohexylalanine (Cha), aminophenylbutyric acid (Pba), phenylalanines mono- and di-substituted at the ortho, meta and para positions of the aromatic ring with one or more of the following groups: β-2- and 3-thienylalanine, β-2- and 3-furanylalanine, β-2-, 3- and 4-pyridylalanine, β-(1- or 2-naphthyl)alanine, serine, threonine and tyrosine O-alkylated derivatives, S-alkylated cysteine, S-alkylated homocysteine, ε-alkylated lysine, δ-alkylated ornithine, αα-dimethylglycine (Aib), α-aminocyclopropane-carboxylic acid ($Ac_3c$), α-aminocyclobutanecarboxylic acid ($Ac_4c$), α-aminocyclopentanecarboxylic acid ($Ac_5c$), α-aminocyclohexanecarboxylic acid ($Ac_6c$), diethylglycine (Deg), dipropylglycine (Dpg), diphenylglycine (Dph), dehydroalanine (δ-Ala), dehydrotyrosine (δ-Tyr) and dehydroleucine (δ-Leu), β-alanine (β-Ala), 2,3-diaminopropionic acid (Dap). Other non-proteic amino acids are those described in: "Diversity of Synthetic Peptides", Konishi et al., First International Peptide Symposium, Kyoto, Japan, 1997.

Examples of hydrophobic amino acids, both natural and non-natural, of L or D configuration, are: glycine, alanine, valine, leucine, isoleucine, methionine, phenylalanine, tyrosine, tryptophan, proline, norleucine, norvaline, alloisoleucine, allothreonine, thioproline, dehydroproline, pipecolic acid, azetidinic acid, cyclohexylglycine (Chg), α-amino-n-butyric acid (Aba), cyclohexylalanine (Cha), phenylalanines mono- and di-substituted at the ortho, meta and para positions of the aromatic ring with one or more of the following groups: β-2- and 3-thienylalanine, β-2- and 3-furanylalanine, β-2-, 3- and 4-pyridylalanine, β-(1- or 2-naphthyl)alanine, serine, threonine and tyrosine O-alkylated derivatives, S-alkylated cysteine, S-alkylated homocysteine, ε-alkylated lysine, δ-alkylated ornithine,α,α-dimethylglycine (Aib), α-aminocyclopropanecarboxylic acid (Ac$_3$c), α-aminocyclobu-tanccarboxylic acid (Ac$_4$c), α-aminocyclopentanecarboxylic acid (Ac$_5$c), α-aminocyclohexanecarboxylic acid (Ac$_6$c), diethylglycine (Deg), dipropylglycine (Dpg), diphenylglycine (Dph), dehydroalanine (δ-Ala), dehydroleucine (δ-Leu). Other non-proteic amino acids are those described in: "Diversity of Synthetic Peptides", Konishi et al., First International Peptide Symposium, Kyoto, Japan, 1997.

Examples of basic amino acids, both natural and non-natural, of L or D configuration, are: histidine, arginine, ornithine, lysine, aminophenylbutyric acid (Pba), ε-alkylated lysine, δ-alkylated ornithine, 2,3-diaminopropionic acid (Dap), 2,4-diaminobutyric acid (Dab). Other non-proteic amino acids are those described in: "Diversity of Synthetic Peptides", Konishi et al., First International Peptide Symposium, Kyoto, Japan, 1997.

The compounds of general formula I can also be used in combination with suitable counterions, as far as they are compatible with the specific applications.

The compounds of the invention can be synthesized with the various techniques known in literature, see for example Schroeder et al., "The Peptides" vol 1, Academic Press, 1965; Bodanszky et al., "Peptide Synthesis" Interscience Publischer, 1966; Barany & Merrifield, "The peptides; Analysis, Synthesis, Biology", 2, Chapter 1, Academic Press, 1980. These techniques include peptide synthesis in solid phase, peptide synthesis in solution, organic chemistry synthetic procedures, or any combination thereof. The selected synthetic scheme will of course depend on the composition of the specific molecule.

Preferably, synthetic procedures based on appropriate combinations of techniques in solid phase and of conventional methods in solution will be used, which involve low production costs particularly on the industrial scale. In more detail, said procedures consist of:

i) Synthesis in solution of fragments of the peptide chain through the successive coupling of N-protected amino acids, suitably activated, with an amino acid or a C-protected peptide chain, recovery of the intermediates, successive selective deprotection of the N and C-terminus of said fragments and coupling of them until obtaining the desired peptide. Finally, when necessary, the side chains are deprotected.

ii) Synthesis in solid phase of the peptide chain from the C-terminus towards the N-terminus on an insoluble polymeric support. The peptide is removed from the resin by hydrolysis with anhydrous hydrofluoric acid or with trifluoroacetic acid in the presence of suitable scavengers, with the concomitant deprotection of the side chains. Particularly preferred sequences are the following:

Particularly preferred sequences are the following:
1. Ace-FAYIARPLPRAHIKEYFY-NH$_2$(SEQ ID NO:1)
2. Ace-CFAYIARPLPRAHIKEYFY-NH$_2$ (SEQ ID NO: 2)
3. FAYIARPLPRAHIKEYFY-NH$_2$ (SEQ ID NO:3)
4. CFAYIARPLPRAHIKEYFY-NH$_2$ (SEQ ID NO:4)

5. CFAYIARPLPRAHIKEYFY-NH$_2$ (SEQ ID NO:5)
   |
   CFAYIARPLPRAHIKEYFY-NH$_2$ (SEQ ID NO:5)

6. Ace-YFYEKIHARPLPRAIYAFC-NH$_2$ (SEQ ID NO:6)

7. YFYEKIHARPLPRAIYAFC-NH$_2$ (SEQ ID NO:7)
   |
   YFYEKIHARPLPRAIYAFC-NH$_2$ (SEQ ID NO:7)

8. FAYIARPLPRAHIKEYF-NH$_2$
9. AYIARPLPRAHIKEY-NH$_2$ (SEQ ID NO:8)
10. CFAYIARPLPRAHIK-NH$_2$ (SEQ ID NO:10)
11. CFAYIARPLPRAHIKE-NH$_2$ (SEQ ID NO:1)
12. FAYIARPLPRAHIK-NH$_2$ (SEQ ID NO:12)
13. PCCFAYIARPLPRAHIKE-NH$_2$ (SEQ ID NO:13)
14. YIARPLPRAHIKEYFYTS-NH$_2$ (SEQ ID NO:14)
15. CFAYIARPLPRAH-NH$_2$ (SEQ ID NO:15)
16. CFAYIARPLPRA-NH$_2$ (SEQ ID NO:16)
17. FAYIARPLPRAH-NH$_2$ (SEQ ID NO:17)
18. CCFAYIARPLPRAHIKEY-NH$_2$ (SEQ ID NO:18)

19. CFAYIARPLPRAHIKEYFYTSGKC (SEQ ID NO:19)
    |_____|

The sequences No 1,2, 5 and 6 are particularly preferred.
The amino acids of peptide No 6 preferably belong to the D series.

Said sequences and peptides can be inserted in or bound to sequences of physiological proteins which act as non-toxic carriers for the antiviral domain, more specifically HIV-suppressive.

Examples of physiological proteins are human albumin or the fragment Fc γ of human immunoglobuline IgG.

The NH$_2$ and COOH terminus can be functionalized so as to make the peptides more resistant to proteases, or the peptides can be cyclized.

Some peptides of the invention have been tested to verify their inhibitory activity against HIV virus-1. Two different tests have been used: the "cell-free " acute infection test and the test of inhibition of the formation of syncitia. The first test evaluates the growth of HIV-1 in primary mononuclear cells pre-activated in vitro and is closer to the natural model of infection. On the other hand, the test of syncitia inhibition evaluates the capability of an inhibitor to inhibit the membrane fusion induced by HIV and it makes use of cells of a continuous line T CD4+ (PM1) chronically infected with an HIV-1 CCR5-dependent (PM1BaL) strain. In both tests, cells were pre-treated with the peptides before exposition to the virus or to 5 the infected cells. Scalar concentrations for each peptide have been tested to calculate the 50% inhibitory dose ($ID_{50}$), i.e. the dose capable of reducing by 50% the values of the untreated controls. The $ID_{50}$ values (expressed as micromolar values) of different peptides in the acute infection test are illustrated in the following Table:

TABLE

| No. | Region | Peptide sequence | ID$_{50}$ |
|---|---|---|---|
| A | RANTES Y27-A38 | (SEQ ID NO: 20) YFYTSGKCSNPA | >150 |
| B | RANTES Y29-V40 | (SEQ ID NO: 21) YTSGKCSNPAVV | >150 |
| C | RANTES S31-V42 | (SEQ ID NO: 22) SGKCSNPAVVFV | >150 |
| 1 | *ac-RANTES F12-Y29-am* | (SEQ ID NO: 1) Ace-FAYIARPLPRAHIKEYFY-NH$_2$ | 11 |
| 2 | *ac-RANTES C11-Y29-am* | | |
| 3 | RANTES C11–C34 | (SEQ ID NO: 2) Ace-CFAYIARPLPRAHIKEYFY-NH$_2$ | 9 |
| | (cyclic) | (SEQ ID NO: 19) CFAYIARPLPRAHIKEYFYTSGKC | 33 |

As it can be seen in the Table, the two peptides ac-RANTES F12-Y29-am and ac-RANTES C11-Y29-am (n. 1–2) showed a marked increase in the capability to, inhibit the acute infection by CCR5-dependent HIV-1BaL strain (i.e. a lower ID$_{50}$). Other peptides of RANTES, used as controls (A, B, C), showed no antiviral activity at the tested doses. Conversely, a cyclic peptide RANTES C11–C34 showed a good inhibitory activity. According to what observed in the acute infection test, the peptides n. 1 and 2 also showed an increased capability to inhibit the formation of syncitia in the system of the PMI line infected by HIV-1BaL.

The peptides of the invention are not capable of inducing activation of the CCR-5 receptor and therefore they induce no toxic pro-inflammatory effects.

The peptides of the invention, the derivatives thereof, or the chimeric proteins in which they are contained, can be used for the therapy or the prophylaxis of AIDS and of other diseases which are caused by the infection of primate lentiretrovirus and of other viruses which use chemokine receptors as membrane receptors. The peptides of the invention can be used for the treatment of allergic or autoimmune diseases, or for the treatment of any other disease in the pathogenesis and clinical manifestations of which the chemokines are involved. The peptides of the invention will be administered suitably formulated in pharmaceutical compositions, for example as reported in "Remington's Pharmaceutical Sciences Handbook", Mack Publishing Company, New York, U.S.A.

The compositions of the invention will contain an effective amount of the peptides (or the derivatives thereof and the chimeric proteins), for instance from 0.1 to 100 mg of peptide, and they will be administered preferably by the parenteral route, in particular by the subcutaneous or intramuscular routes. The daily amount will obviously depend on different factors, like severity of the disease, weight, sex and age of the patient, and it will be determined on the basis of the toxicological, pharmacokinetic and pharmacodynamic properties of each single peptide or derivative thereof. Generally the peptide daily dosage will be comprised between 10 and 1500 μmol per Kg of body weight and the treatment will be maintained for a long time. Also other administration routes can be used, for example the oral route using liposome formulations or other techniques known for the administration of peptides or proteins by the gastro-enteric route, as described in WO93/25583.

Further, the peptides of the invention can be used for the production of anti-peptide antibodiesand antuidiotype antibodies raised to the anti-peptide antibody, which anti-idiotype antibodies simulate the original peptide through their active site; for the development of peptide mimetics with antiviral activity or for the development of antagonists of the chemokine receptor.

Such antibodies, optionally human antibodies, have a favorable diffusion and stability and a longer half life in vivo.

The techniques used for the production of antuidiotype antibodies and human antibodies are described for example in WO 86/1539 and in EP-A-481790.

The peptides of the invention are useful also as diagnostic and research tools, for instance for the structural characterization of the active site by means of computer aided-molecular design, crystallography or NMR.

The following examples illustrate the invention in greater details.

EXAMPLE 1

Synthesis of the peptide Ace-Phe-Ala-Tyr-Ile-Ala-Arg-Pro-Leu-Pro-Arg-Ala-His-Ile-Lys-Glu-Tyr-Phe-Tyr-NH$_2$, corresponding to the compound of general formula (I) wherein: X1=Ace; X2=Phe; X3=Ala; X4=Tyr; X5=Ile; X6=Ala; X7=Arg; X8=Pro; X9=Leu; X10=Pro; X11=Arg; X12=Ala; X13=His; X14=Ile; X15=Lys; X16=Glu; X17=Tyr; X18=Phe; X19=Tyr; X20=NH$_2$.

This compound was prepared by peptide synthesis in solid phase. In particular, the methodology which makes use of the a-amino-protecting Fmoc group. Furthermore, said synthesis was carried out using an automatic peptides synthesizer which operates in continuous flow. The synthesis was carried out using a solid support which provides the peptide as C-terminus amide. A 0.2 mmol synthetic scale was made use of, using a resin substitution equivalent to 0.50 mmol/g. The α-amino-protecting Fmoc group of each residue, after coupling, was removed by means of a 20% by volume solution of piperidine in DMF. Two successive treatments of 3 and 7 minutes, respectively, were used for each cycle. Amino acids have been bound in successive steps, and the conditions and the methodologies used for each single residue are those conventionally used in this synthesis.

After completion of the synthesis the N-terminus was acetylated by treatment with a 20% by volume solution of acetic anhydride in DMF. 10 ml of said solution were used and the treatment was carried out for 20 minutes. The peptide was removed from the resin simultaneously with the side chain protecting groups, by means of an ethanedithiol/anisole/TFA mixture in a 0.25/0.25/9.5 ratio (by volume) at 0° C. for 2 h. The resin was filtered, and the crude peptide was precipitated from the acidic solution with ethyl ether. 0.193 g of crude product were obtained in the form of powder. A 42% yield was obtained, based on the resin substitution degree. The homogeneity of the product was evaluated by analytical HPLC, and it showed a single main peak at tr=16.5. The crude material was purified by preparative RP-HPLC. 0.038 g of pure product were obtained. The analytical HPLC confirmed the purity of the product. The identity of the product was confirmed by MALDI-TOF mass spectrometry, which confirmed the expected molecular weight of 2294 μma.

EXAMPLE 2

According to the same method of example 1, the following peptides were obtained:

a) Ace-CFAYIARPLPRAHIKEYFY (SEQ ID NO:2); mw-2400 Assay >95% b) Ace-YFYEKIHARPLPRAIYAFC (SEQ ID NO:6); MW=2400 Assay >95%

Peptide b) consists of D-amino acids and its sequence corresponds to the inverted sequence of peptide a).

EXAMPLE 3

Inhibition of the Viral Infection

The ability of the mutants obtained as described in Example 2, to inhibit the infection by the prototypic macrophage-tropic HIV-1BaL strain, was evaluated in primary cultures of activated mononuclear cells from peripheral blood. The procedure used to infect PBL and to evaluate the production of p24 antigen is described in literature (Scarlatti et al., Nat. Med. November 3:11 1259–65, 1997).

What is claimed is:

1. An isolated peptide consisting of an amino acid sequence selected from the group consisting of Ace-FAYIARPLPRAHIKEYFY-NH$_2$ (SEQ ID NO:1),
Ace-CFAYIARPLPRAHlIKEYFY-NH$_2$ (SEQ ID NO:2),
FAYIARPLPRAHIKEYFY-NH$_2$ (SEQ ID NO:3),
CFAYIARPLPRAHIKEYFY-NH$_2$ (SEQ ID NO:4), CFAYIARPLPRAHIKEYFY-NH$_2$ (SEQ ID NO:5)
|
CFAYIARPLPRAHIKEYFY-NH$_2$ (SEQ ID NO:5), FAYIARPLPRAHIKEYF-NH$_2$ (SEQ ID NO:8),
AYIARPLPRAHIKEY-NH$_2$ (SEQ ID NO.9),
CFAYIARPLPRAHIK-NH$_2$ (SEQ ID NO:10),
CFAYIARPLPRAHIKE-NH$_2$ (SEQ ID NO:11),
FAYIARPLPRAHIK-NH$_2$ (SEQ ID NO:12),
CFAYIARPLPRAH-NH$_2$ (SEQ ID NO:15),
CFAYIARPLPRA-NH$_2$ (SEQ ID NO:16), and
FAYIARPLPRAH-NH$_2$ (SEQ ID NO:17).

2. A composition containing as active principle at least one peptide of claim 1.

3. A method of treating HIV comprising administering an effective amount of at least one peptide of claim 1 to an individual in need of said treating, said method resulting in an increase in the capability to inhibit an acute infection of HIV.

4. A method of treating HIV comprising administering a composition of claim 2 to an individual in need of said treating, said method resulting in an increase in the capability to inhibit an acute infection of HIV.

* * * * *